June 14, 1960 R. S. MOORE Plant Pat. 1,952
MINIATURE ROSE PLANT
Filed Aug. 24, 1959
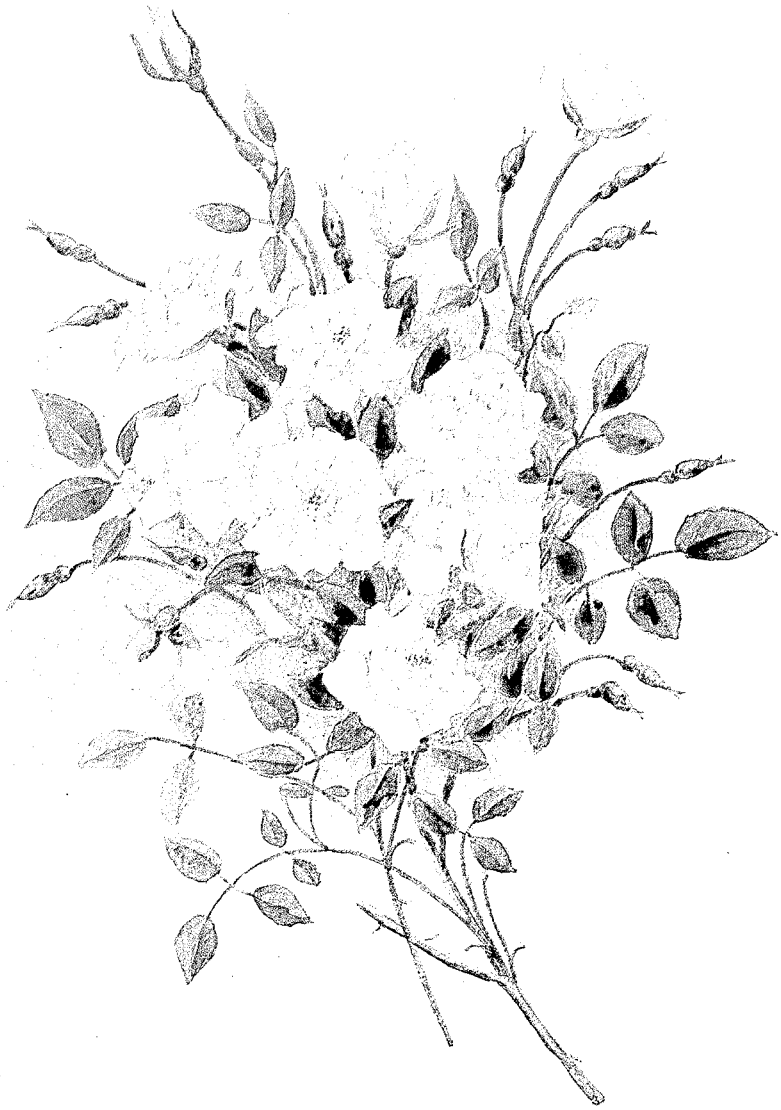
WITNESS
Addison E Avery
INVENTOR
Ralph S. Moore
Webster & Webster
ATTYS.

United States Patent Office

Plant Pat. 1,952

Patented June 14, 1960

1,952

MINIATURE ROSE PLANT

Ralph S. Moore, 2519 E. Mineral King, Visalia, Calif.

Filed Aug. 24, 1959, Ser. No. 835,808

1 Claim. (Cl. 47—61)

This invention relates to a new and distinct variety of miniature rose plant which is dwarf, very bushy, and extremely free-flowering; the variety being particularly characterized by buds which resemble a Hybrid Tea rose, and which buds—after the calyx breaks—are an attractive soft butterscotch or straw-yellow color, which shade is carried into the newly opened flowers, but which later turn a substantially full white.

The present variety of miniature rose plant generally resembles the Bit O'Sunshine rose (United States Plant Patent No. 1,631) in the shape of the bud and habit of growth of the plant, but—in comparison—the flowers are more double, with a substantially greater number of petals, and the foliage is a darker green color.

Additionally, as characteristic features, the plant of the present variety grows well in a pot or in the garden, blooms good outdoors or indoors, reaches a maximum height of only twelve to fourteen inches at maturity, and roots readily from soft wood cuttings.

The variety was originated by me, in my nursery located at Visalia, California, and under conditions of careful control and observation, as a cross between Golden Glow (United States Plant Patent No. 263) as the seed parent, and Zee (unpatented) as the pollen parent.

Subsequent to origination of the variety I successfully asexually reproduced it, in my nursery located as aforesaid, by cuttings; the reproductions having run true in all respects.

The figure of the drawing illustrates a spray, including foliage, buds, and flowers.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Dwarf; bush; seedling; cut flowers; garden decoration.

Class: Hybrid miniature.

*Flowers*

Continuity: Continuous.

Fragrance: Moderate.

Flowers borne: Singly to several to stem, in irregular cluster on normal strength, medium length stems.

Quantity of bloom: Free, both outdoors and in greenhouse.

Bud:

*Peduncle.*—Long; slender; medium; erect. Color—green. Smooth.

*Before calyx breaks.*—Size—small. Color—green.

*As calyx breaks.* — Color — straw yellow (604/2 British Colour Council).

*As first petal opens.*—Color: Outside—straw yellow (604/2 British Colour Council); inside—straw yellow (604/2, shading to 604/1 at base—British Colour Council. Opening—opens well at all times.

Bloom:

*Size when fully open.*—Small, average 1¼" to 1½".

*Petalage.*—Very double, with from fifty to sixty petals arranged regularly.

*Form.*—High center at first; petals remaining at first loosely rolled outward, becoming later—at maturity—tightly rolled outward.

Petals: Thin; soft; satiny both inside and outside.

*Shape.*—Lanceolate.

*Color.*—Newly opened flower from plant grown in a greenhouse—Outside petal: Outside surface—Chinese yellow (606/3 British Colour Council); inside surface—Straw yellow (604/3 British Colour Council). Intermediate petal: Outside surface—Chinese yellow (606/3 British Colour Council); inside surface—Straw yellow (604/3 British Colour Council). Inner petal, Outside surface—Straw yellow (604/3 British Colour Council); inside surface—Straw yellow (604/3 British Colour Council). A flower that was open for three days in a greenhouse——all petals—substantially full white.

*General color effect.*—Newly opened flower—Straw yellow (604/3 British Colour Council); three days open—substantially full white.

*Behavior.*—Drop off cleanly.

*Flower longevity.*—Bush in garden—two to four days. Cut flowers grown outdoors or in a greenhouse and kept at room temperatures—two to three days.

*Reproductive organs*

Stamens: None to very few.

Filaments: Short; color—white to light green; most without anthers.

Pollen: None in summer; sometimes abundant in spring. Color—yellow.

Pistils: Few.

Styles: Uneven; short; bunched.

Stigma: Pale yellow-green, with some red shading.

Ovaries: All enclosed in calyx.

Hips: None.

Sepals: Long; spear shaped; recurved. Color—green.

Seeds: None.

*Plant*

Foliage:

*Leaves.*—Compound of five leaflets; normal abundance; small; thin; leathery; slightly glossy.

*Leaflets.* — Shape — lanceolate, with apex acute. Base—round.

*Color.* — Mature leaves; Upper surface — normal green (22–L–8 Maerz and Paul); under surface—lighter normal green (21–D–6 Maerz and Paul). Young leaves: Upper surface — normal green; under surface—normal green with slightly red cast.

*Rachis.* — Medium; upper side — smooth, grooved; under side—a few thorns, three to four.

*Stipules.*—Short, with short points turning out at an angle of more than 90 degrees.

Growth:

*Habit.*—Dwarf; bushy.

*Growth.*—Vigorous.

*Canes.*—Light.

*Main stems.*—Color—green. Thorns—few; medium length; straight to hooked slightly downward, with short narrow base. Prickles—few. Hairs—none.

*Branches.* — Color — Green (19–L–7 Maerz and Paul). Thorns—few; short; straight. Color—brown (4–A–11, shading to pale green at point—Maerz and Paul). Prickles—none. Hairs—none.

*New shoots.*—Color—green to bronze red. Thorns—few; short; straight. Prickles—none. Hairs—none.

The miniature rose plant and its flowers are herein described may vary in slight detail due to climatic and soil conditions under which the variety may be grown; the present description being of the variety as grown at Visalia, California.

The following is claimed:

A new and distinct variety of dwarf, very bushy, extremely free-flowering, miniature rose plant having buds which resemble a Hybrid Tea rose, and which buds—after the calyx breaks—are an attractive soft butterscotch or straw yellow color, which shade is carried into the newly opened flowers but which later turn substantially full white; the variety generally resembling the Bit O'Sunshine rose in the shape of the bud and habit of growth of the plant, but—in comparison—the flowers are more double, with a substantially greater number of petals, and the foliage is a darker green color; and further characterized by a plant which grows well in a pot or in the garden, blooms good indoors or outdoors, normally reaches a maximum height of twelve to fourteen inches at maturity, and roots easily from soft wood cuttings.

No references cited.